United States Patent [19]

Walker

[11] 4,351,325
[45] Sep. 28, 1982

[54] HERNIA SUPPORT

[76] Inventor: Trevor E. Walker, Con Amore, St. Georges Rd., Donnington, Shropshire, England

[21] Appl. No.: 222,551

[22] Filed: Jan. 5, 1981

[51] Int. Cl.³ .............................................. A61F 5/24
[52] U.S. Cl. .................................. 128/96; 128/119
[58] Field of Search ............... 128/96, 99, 101, 106, 128/112, 119

[56] References Cited

U.S. PATENT DOCUMENTS

| | | | |
|---|---|---|---|
| 731,141 | 6/1903 | Tirrill et al. | 128/119 |
| 1,221,016 | 4/1917 | Best | 128/119 |
| 2,469,260 | 5/1949 | Chalk | 128/96 |
| 2,586,219 | 2/1952 | Geffas | 128/119 |
| 2,613,669 | 10/1952 | Haesly | 128/119 |

Primary Examiner—John D. Yasko
Attorney, Agent, or Firm—LeBlanc, Nolan, Shur & Nies

[57] ABSTRACT

Support, particularly for inguinal hernias, comprises a "roll-on" belt to which a pressure pad for bearing on the area of the hernia is indirectly attached by an arrangement including a rigid stay member. A strap extends from a lower edge of the pad between the wearer's legs to keep the pad pressed against the body by reaction with the rigid stay even when movement tends to displace the adjacent part of the belt away therefrom e.g. when sitting or stooping.

7 Claims, 3 Drawing Figures

HERNIA SUPPORT

DESCRIPTION

This invention relates to supports for hernias, in particular inguinal hernias, and has as its object the provision of a support which is effective, comfortable and secure in use.

According to the invention a hernia support includes a belt for securely encircling the wearer's body including the area of the hernia in use, a pad within the belt shaped to bear on said area and having a strap extending from a lower edge portion to pass between the wearer's legs in use and secured in the region of the wearer's back, and a substantially rigid stay member located between the pad and the belt with a first flexible connection between its upper edge and a transverse upper region of the outer face of the pad and a second flexible connection between its lower edge and the belt inner face, whereby movement tending to displace the belt upwards and/or outwardly from said area is accompanied by angling of the stay in reaction to the pull of said strap thereby urging the pad inwards to maintain or increase its operative pressure on said area.

A practical example of the invention is now more particularly described with reference to the accompanying drawings, wherein.

Figure 1:
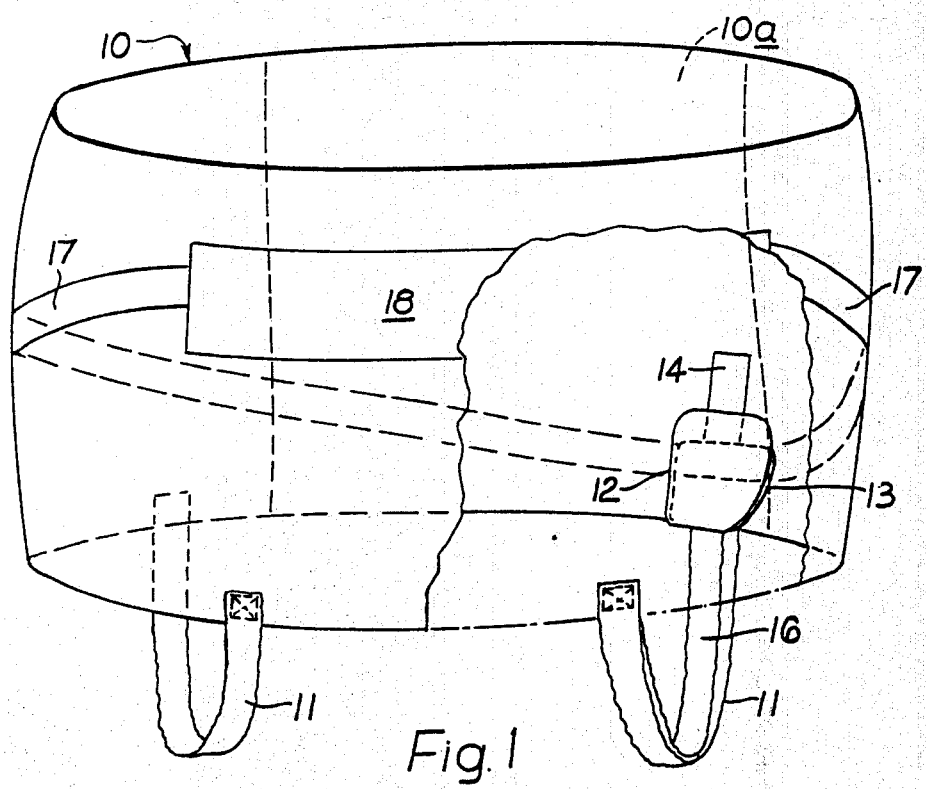
FIG. 1 is a rear perspective view of a support for a right inguinal hernia with part of the rear of its belt broken away.
Figure 3:
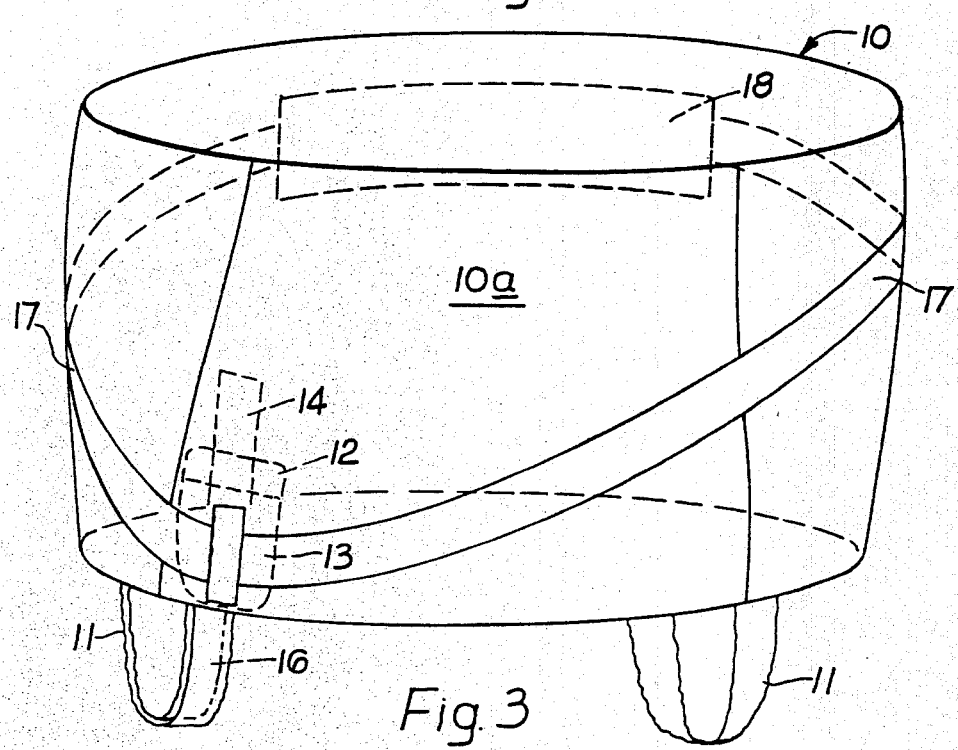
FIG. 3 is a front perspective view of the support.

The support comprises an elasticated girdle or "roll on" type of belt 10 of generally known design per se having a non-resilient front reinforcement panel 10a and about 170 mm in height so as to fit closely around the lower body of a wearer from the waist over the hips. A pair of elasticated leg straps 11 attached to the lower margin of the belt prevent its lower edge riding up in use.

A pad 12 has a stiff plastics core or backing enclosed in fabric and is trapezoidal in outline with rounded corners, haaving parallel top and bottom edges, a left edge (as viewed by the wearer) generally vertical and an angled right edge so that it tapers towards the bottom for close fit adjacent to the wearers right thigh at the right inguinal region, said pad being some 70 mm high and 60 mm in maximum width.

This pad is not directly mounted on belt 10, between it and the front interior wall of the belt is located a flat stay 13 coextensive with approximately the lower ¾ of the height of pad 12.

Figure 2:
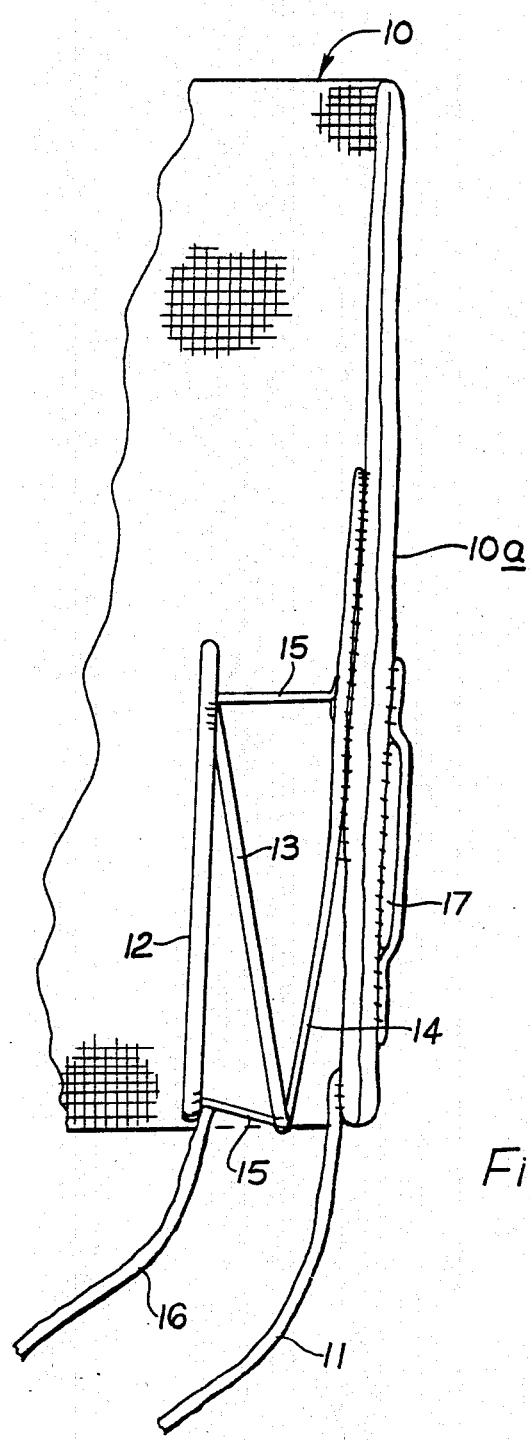
FIG. 2 is a vertical section through the belt and a pad and stay of the support.

The lower edge of stay 13 is connected to the adjacent lower region of belt 10 by a flexible non-elastic tape 14 (FIG. 2) and is hinged at its top edge to the front face of pad 10 by flexible material. Limit tapes 15 with a free length of about 20 mm connect the lower edges of pad 12 and stay 13 loosely together, likewise the upper edge of the latter and the opposing face of belt 10. In FIG. 2 the pad is shown pulled away from belt 10 to the maximum extent to show these tapes more clearly.

An elasticated tension strap 16 is attached to the lower edge of pad 12 to pass between the wearer's legs to an anchorage at the back of the belt common with the right hand leg strap 11.

Reinforcement and more positive location of the anchorage area of the pad and stay assembly is provided by a pair of downwardly converging webbing outer straps 17 stitched through the belt at their lower ends to form a positive connection with tape 14. Straps 17 pass upwardly and rearwardly about the hips of the wearer and are attached to an elastic transverse back strap 18 stitched at its centre only to the central upper part of the belt back so that it can expand independently of the belt to maintain tension on straps 17.

Worn as described the "sandwich" arrangement of pad 12, stay 13 and belt 10 aided by the location afforded by the strap arrangements provide secure and steady pressure on the inguinal region when the user is in an erect posture, as in the case with many known types of truss or other rupture support. However it is a shortcoming of many of the known devices that in other postures, particularly when the body is bent at the hips as when sitting, squatting or stooping; or during active movement, this pressure is not maintained (possibly when the support is most needed) as the critical area of the belt or other locating device is displaced away from the inguinal region e.g. by movement of the user's thigh.

With the present invention this effect is avoided or largely minimised in that such movement of belt 10 does not directly affect the positioning of pad 12 as the latter is not mounted directly thereon. Instead the reaction between the downward pull of elastic tension strap 16 and the upward location of straps 17 puts stay 13 in vertical compression displacing it angularly towards the position shown in FIG. 2 and urging the upper part of pad 12 firmly into even more close contact with the inguinal region, its lower part being held in such contact by the pull on strap 16. In this way evenly distributed inward pressure is maintained by pad 12 whatever the position of the body.

To make the support easier to put on and more comfortable in wear the two leg straps 11 may be brought together at the back and attached to the centre rear region of belt 10 in common with tension strap 16, though all these straps are quite separate to the front as shown in the drawing. They are preferably provided with soft covering sleeves, and may be contained in a common sleeve extending some 75 mm. from said belt rear region.

I claim:

1. A herina support including a belt for securely encircling the wearer's body including an area comprising and substantially surrounding the hernia in use, a pad within the belt having an inner face shaped to bear evenly on the whole of said area and having a strap extending from a lower edge portion of the pad to pass between the wearer's legs in use and secured to the belt in the region of the wearer's back, and a substantially rigid stay member located between the pad and the belt inner face with a first flexible connection between its upper edge and a transverse upper region of the outer face of the pad and a second flexible connection between its lower edge and the belt inner face, whereby movement tending to displace the belt upwards and/or outwardly from said area is accompanied by angling of the stay in reaction to the pull of said strap thereby urging the pad away from the belt inner face to maintain or increase operative even pressure of the pad on the whole of said area.

2. A support has in claim 1 wherein the belt is an elasticated girdle having a non-resilient front reinforcement panel and shaped to fit closely around the lower body of a wearer from the waist over the hips.

3. A support as in claim 2 including a pair of leg straps attached to a lower margin of the belt to prevent riding up in use.

4. A support as in claim 1, 2 or 3 wherein the second flexible connection is a flexible non-elastic tape connecting a lower edge of the stay to an adjacent lower region of the belt.

5. A support as in claim 1 including flexible limit elements loosely connecting a lower edge region of the pad with a lower edge region of the stay and an upper edge region with an opposing part of the belt to limit displacement of the pad away from the belt interior.

6. A support as in claim 1 wherein the strap is elasticated.

7. A support as in claim 1 including strap means connected with the area of anchorage of the assembly of pad and stay to the belt to pass over the wearer's hips, being attached to a central upper part of the back of the belt through elasticated tension means.

* * * * *